(12) United States Patent
Armstrong

(10) Patent No.: US 9,655,883 B2
(45) Date of Patent: May 23, 2017

(54) PHARMACEUTICAL COMPOSITION

(75) Inventor: David Nigel Armstrong, Atlanta, GA (US)

(73) Assignee: SLA PHARMA AG (CH)

( * ) Notice: Subject to any disclaimer, the term of this patent is extended or adjusted under 35 U.S.C. 154(b) by 946 days.

(21) Appl. No.: 12/834,198

(22) Filed: Jul. 12, 2010

(65) Prior Publication Data
US 2010/0305178 A1 Dec. 2, 2010

Related U.S. Application Data

(63) Continuation of application No. 10/525,208, filed as application No. PCT/GB03/03692 on Aug. 22, 2003, now abandoned.

(60) Provisional application No. 60/406,351, filed on Aug. 26, 2002.

(51) Int. Cl.

| | | |
|---|---|---|
| *A01N 45/00* | (2006.01) |
| *A61K 31/56* | (2006.01) |
| *A61K 31/4164* | (2006.01) |
| *A61K 9/00* | (2006.01) |
| *A61K 31/192* | (2006.01) |
| *A61K 31/24* | (2006.01) |
| *A61K 31/245* | (2006.01) |
| *A61K 31/355* | (2006.01) |
| *A61K 31/407* | (2006.01) |
| *A61K 31/4166* | (2006.01) |
| *A61K 31/545* | (2006.01) |
| *A61K 31/573* | (2006.01) |
| *A61K 31/60* | (2006.01) |
| *A61K 31/65* | (2006.01) |
| *A61K 33/30* | (2006.01) |
| *A61K 45/06* | (2006.01) |
| *A61K 47/06* | (2006.01) |
| *A61K 47/44* | (2017.01) |
| *A61K 9/06* | (2006.01) |

(52) U.S. Cl.
CPC ........ *A61K 31/4164* (2013.01); *A61K 9/0014* (2013.01); *A61K 9/0031* (2013.01); *A61K 9/06* (2013.01); *A61K 31/192* (2013.01); *A61K 31/24* (2013.01); *A61K 31/245* (2013.01); *A61K 31/355* (2013.01); *A61K 31/407* (2013.01); *A61K 31/4166* (2013.01); *A61K 31/545* (2013.01); *A61K 31/573* (2013.01); *A61K 31/60* (2013.01); *A61K 31/65* (2013.01); *A61K 33/30* (2013.01); *A61K 45/06* (2013.01); *A61K 47/06* (2013.01); *A61K 47/44* (2013.01)

(58) Field of Classification Search
CPC .............. A61K 31/4164; A61K 9/0014; A61K 9/0031; A61K 31/192; A61K 31/24
USPC .......................................................... 514/171
See application file for complete search history.

(56) References Cited

U.S. PATENT DOCUMENTS

| | | |
|---|---|---|
| 4,784,994 A | 11/1988 | Romer et al. |
| 4,957,918 A | 9/1990 | Martin et al. |
| 5,248,505 A | 9/1993 | Garwin |
| 2003/0092754 A1 | 5/2003 | Nishimuta et al. |

FOREIGN PATENT DOCUMENTS

| | | |
|---|---|---|
| CN | 1291484 | 4/2001 |
| RU | 119610523913 | 6/1998 |
| UA | 53946 | 2/2003 |
| WO | 92/09272 | 11/1992 |

OTHER PUBLICATIONS

Willis et al. (Metronidazole in prevention and treatment of bacteroides infections after appendicectomy. Br Med J. Feb. 7, 1976; 1(6005): 318-321.).*
Huber, L., "Role of Klion Ointment in the Treatment of Crural Ulcer," Therapia Hungarica, 39(3), 148-150 (1991).
Teknologiya Lekarstvennye Form, edited by Kondrat'jeva, T.C., pp. 282-285 and 314-317, Medisina, Moscow 1991 & English Translation.
Kryzhanovsky, S.A. et al., Sovremennye Lekarstvennye Preparaty, p. 792, Ripol Classic—Moscow, 2000 & English Translation.
Urbanek et al., Vulval Crohns Disease Difficulties in Diagnosis, pp. 211-214, 996 May 21(3).
Ursing et al., Metronidazole for Chrohn's Disease, Lancet, 1975.1 (7910)775-777.

* cited by examiner

*Primary Examiner* — Layla Soroush
(74) *Attorney, Agent, or Firm* — Marianne Fuierer; Moore & Van Allen, PLLC

(57) ABSTRACT

A topical composition comprises at least 5-wt % metronidazole or a pharmacologically acceptable derivative thereof in a non-aqueous vehicle. The composition may be used in the treatment of conditions of the colon, rectum, anorectum and perianal region, in particular inflammatory bowel disease and perianal Crohn's disease. The composition also relieves pain and inflammation and promotes healing of the colon, rectum, and anorectum and perianal region following surgical operations. One advantage of the composition is that topical administration of metronidazole results in a primarily local effect and thus side effects observed from systemic administration are avoided.

25 Claims, No Drawings

PHARMACEUTICAL COMPOSITION

This is a continuation application of U.S. application Ser. No. 10/525,208, filed Mar. 30, 2006; which is a National Stage Application of PCT/GB2003/003692; filed Aug. 22, 2003; which claims priority to U.S. Provisional Application No. 60/406,351, filed Aug. 26, 2002. All of the above applications are incorporated into the current continuation application by reference.

TECHNICAL FIELD

The present invention relates to a pharmaceutical composition, in particular a topical composition comprising metronidazole or a pharmacologically acceptable derivative thereof. Hereinafter, the term "metronidazole" is to be taken as including pharmaceutically acceptable derivatives thereof unless otherwise apparent from the context.

BACKGROUND OF THE INVENTION

Metronidazole (or "Flagyl") is a synthetic antibacterial and antiprotozoan antibiotic having the formula 2-methyl-5-nitroimidazole-1-ethanol. The antibiotic has been used for many years in its oral or intravenous form, to treat inflammatory conditions of the colon, rectum, anal canal and perianal region. Oral metronidazole has been traditionally used to treat inflammatory bowel disease (including Crohn's disease and ulcerative colitis), idiopathic proctocolitis, or radiation proctitis. In addition, the oral form is used to treat inflammatory conditions of the perianal region or anal canal such as anal fissures, fistulas, abscess, ulcers or post-surgical wounds. Metronidazole is also used in an intravenous form to treat systemic sepsis resulting from several inflammatory conditions of the colon and rectum.

Metronidazole possesses not only anti-bacterial properties, but also anti-inflammatory properties, which are less well understood. The medication is used for its anti-inflammatory properties in the treatment of several skin diseases.

Metronidazole is frequently associated with a number of serious side effects, both in its oral and intravenous form. These include GI manifestations, such as nausea, vomiting, a metallic taste in the mouth, or inflammation of the oral cavity. Serious neurological side effects can occur which usually manifest as numbness or tingling of the extremities. These neurological side effects can be debilitating, are often irreversible, and necessitate stopping the Metronidazole. Serious hematological, cardiovascular, or renal complications are also common and can be life-threatening. In addition, the overgrowth of opportunistic organisms such as Candida can result from oral or intravenous metronidazole treatment. In addition, oral metronidazole can interact in an adverse manner with other medications, such as oral anticoagulants (e.g. coumadin), which can cause potentially fatal bleeding.

Topical metronidazole has previously been used for a number of skin conditions (e.g. rosacea) or as a topical vaginal preparation in the treatment of vaginal infections (e.g. trichomonas). These preparations are contained in a medium containing alcohol, which would result in stinging and burning when used in the perianal region or in the anal canal. As far as the inventor is aware, there is no disclosure of the direct application of metronidazole into the rectum or distal colon (as for example a suppository, foam or enema) in the treatment of inflammatory disease and no such preparation of metronidazole is commercially available.

DESCRIPTION OF THE INVENTION

It is, therefore, an object of preferred embodiments of the present invention to administer metronidazole to treat certain conditions of the distal GI tract avoiding these unwanted side effects.

According to the first aspect of the present invention, there is provided a topical composition comprising metronidazole or a pharmacologically acceptable derivative thereof at a concentration of at least about 5 wt % in a pharmacologically acceptable non-aqueous vehicle. The concentration of metronidazole is preferably between from about 5 wt % to about 50 wt %, more preferably between from about 5 wt % to about 15 wt % and most preferably about 10 wt %. The concentrations are based on the total weight of the composition.

The vehicle is preferably an organic vehicle and, typically, comprises at least one hydrocarbon compound. Preferably, the vehicle comprises a mixture of at least two semi-solid saturated hydrocarbon compounds. An example of a suitable vehicle is white petrolatum (USP), also known as white soft paraffin (BP). Other suitable vehicles include zinc oxide, Vaseline™, Aquaphor (a combination of mineral oil, petrolatum ceresin and lanolin), lanolin or a petroleum-based carrier.

The composition may consist essentially of metronidazole and the vehicle. However, a therapeutic amount of at least one other agent may be added to the composition to add to its effectiveness. Additional agents that may be added include steroids, e.g. hydrocortisone or a pharmacologically acceptable derivative thereof, analgesic agents, preferably from the amide or ester class such as pramoxine or benzocaine, antimicrobial agents (antibacterial or antiviral), e.g. ciprocfloxacin, amoxicillin-clavulonic acid, erythromycin, tetracycline, clindamycin or doxycyclin, substances that either promote skin integrity or inhibits skin breakdown, e.g. vitamin E, aloe, zinc oxide or other barrier cream, anti-inflammatory agents, e.g. a non-steroidal anti-inflammatory agent selected from aminosalicylic acid, ibuprofen, sulindac, piroxicam or diflunisal and antidiarrheal compounds such as a bismuth salt. The additional or supplemental antibiotic or antiviral medications may add to the anti-bacterial spectrum of activity (gram positive, gram negative aerobic or anaerobic, antiviral) of metronidazole.

The topical composition is preferably in a form suitable for direct application to the colon, rectum, anorectum, perianal region or anal canal. Suitable forms include an enema, suppository, ointment, lotion, gel, foam or cream. Preferred forms include ointment or enema. The ointment, lotion, gel or cream forms may be used to treat conditions affecting the perianal region and anorectum including perianal Crohn's disease and conditions arising following a hermorrhoidectomy. The suppository, foam or enema forms may be used to treat conditions affecting the colon or rectum including inflammatory bowel disease (Crohn's disease or ulcerative colitis), radiation proctitis, idiopathic proctocolitis or post-surgical pouchitis in a surgically constructed ileal J-pouch. Examples of suitable vehicles for enema formulations include but are not limited to sodium chloride and 1% methylcellulose; propylene glycol and 2% methylcellulose gel; glycerin, 2% methylcellulose gel (retention enema); base C, glycerin, green soap; silica gel (micronized), 2% methylcellulose gel; 2% methylcellulose gel and purified water; sodium chloride, purified water, sodium hydroxide; xanthan gum, purified water, 2% methylcellulose gel; carbopol, xanthan gum; methocel 1%, polsorbate.

According to a second aspect of the present invention, there is provided a topical composition comprising metronidazole or a pharmacologically acceptable derivative thereof at a concentration of at least about 5 wt % in a pharmacologically acceptable non-aqueous vehicle for use in the treatment of the human or animal body.

The inventor has discovered that not only is the composition useful in the treatment of conditions of the colon, rectum, anorectum and perianal region but also that the composition assists in patient recovery following operations of the distal GI tract by relieving pain, reducing inflammation and edema, promoting wound healing and reversing tissue induration and granulation.

According to a third aspect of the present invention, there is provided use of metronidazole or a pharmacologically acceptable derivative thereof in the manufacture of a topical medicament to relieve pain caused by conditions of the colon, rectum, anorectum or perianal region.

According to a fourth aspect of the present invention, there is provided use of metronidazole or a pharmacologically acceptable derivative thereof in the manufacture of a medicament to relieve pain following a surgical operation to the colon, rectum, anorectum or perianal region.

According to a fifth aspect of the present invention, there is provided use of metronidazole or a pharmacologically acceptable derivative thereof in the manufacture of a topical medicament to reduce inflammation following a surgical operation to the colon, rectum, anorectum or perianal region.

According to sixth aspect of the present invention, there is provided use of metronidazole or a pharmacologically acceptable derivative thereof in the manufacture of a topical medicament to promote healing following a surgical operation to the colon, rectum, anorectum or perianal region.

According to a seventh aspect of the present invention, there is provided use of metronidazole or a pharmacologically acceptable derivative thereof in the manufacture of a topical medicament to reduce edema following a surgical operation to the colon, rectum, anorectum or perianal region.

According to an eight aspect of the present invention, there is provided use of metronidazole or a pharmacologically acceptable derivative thereof in the manufacture of a topical medicament to reverse tissue induration and granulation following a surgical operation to the colon, rectum, anorectum or perianal region.

The topical composition appears to be particularly effective where the surgical operation is an anorectal operation. Examples of operations in which the topical composition assists recovery include hemorrhoidectomy, fistulotomy, fissurectomy, sphincterotomy, sphincteroplasty or incision and drainage of an abscess. The invention has particular efficacy following a hemorrhoidectomy.

According to a ninth aspect of the present invention, there is provided use of metronidazole or a pharmacologically acceptable derivative thereof in the manufacture of a topical medicament to treat conditions of the colon, rectum, anorectum or perianal region. Examples of treatable conditions include inflammatory bowel disease, ulcerative colitis, perianal Crohn's disease, radiation proctitis, idiopathic proctocolitis or pouchitis.

According to a tenth aspect of the present invention, there is provided use of metronidazole or a pharmacologically acceptable derivative thereof in the manufacture of a topical medicament to treat anorectal or perianal ulcers or skin defects. The ulcers may be infective or inflammatory ulcers and may be induced by HIV or radiation. The ulcers may be erosive ulcers resulting from chronic diarrhea or anorectal incontinence. The ulcers may be associated with inflammatory bowel disease.

According to an eleventh aspect of the present invention, there is provided use of metronidazole or a pharmacologically acceptable derivative thereof in the manufacture of a topical medicament to treat perianal infective or inflammatory processes. Examples of such processes include perianal abscess, fissure in ano, hindradenitis, pilonidal abscess or sinus.

The medicament may have any or all of the features of the topical composition of the first aspect in any appropriate combination.

The invention also encompasses methods of treatment of the above-mentioned conditions and indications using the topical composition of the first aspect of the present invention. The dose of metronidazole for each application is preferably between from about 125 mg to about 1250 mg, more preferably between from about 125 mg to about 375 mg and most preferably about 250 mg. The most preferred dose is based on a single application of 2.5 $cm^3$ of a 10 wt % metronidazole ointment. The composition is usually applied between from 2 to 4 times daily and preferably 3 times daily.

Without wishing to be bound by any particular theory, the inventor believes that the use of metronidazole in a topical form by direct application to the diseased or otherwise affected area results in a primarily local effect. Minimal systemic absorption is observed and therefore systemic side effects are effectively eliminated. In addition, a greater dose of metronidazole can be applied directly to the diseased or otherwise effected area, so increasing the efficacy of the medication.

Compositions comprising metronidazole in the form of a gel, cream, ointment, lotion, foam or suppository may be used to treat conditions in the lower parts of the anorectum, such as perianal Crohn's disease, postoperative incisions, ulcers, abscess, fissures, or fistulas. In addition, metronidazole can be used in an enema form to treat conditions of the more proximal rectum and colon, such as inflammatory bowel disease, radiation proctitis, idiopathic proctocolitis or post-surgical "pouchitis" in a surgically constructed ideal J pouch.

DETAILED DESCRIPTION

The following is a description of the present invention by way of example only and is not intended to limit the scope of the invention as defined in the claims.

Example 1—Method of Production of the Composition 100 g of metronidazole powder (USP) was mixed with 900 g of white petrolatum (USP) and the mixture passed through a mixer known as an "ointment mill" to produce a 10 wt % metronidazole composition having a "fluffy" texture.

Example 2—Post-Hemorrhoidectomy

Twenty patients with grade 3 or 4 hemorrhoidal disease with significant external components and with or without a fissure in ano were studied. The presence of neurological deficit, chronic pain syndrome, and patients currently taking narcotic analgesics were excluded. All patients gave informed consent prior to involvement in the study. Patients underwent a closed three-quadrant Harmonic Scalpel hemorrhoidectomy under general anesthesia, with the patient in prone jack-knife position. All surgeries were performed by the same surgeon (DNA). In patients requiring fissurectomy and sphincterotomy, the flat blade of the Harmonic Scalpel was utilized to cauterize the fissure, and a left lateral internal sphincterotomy was performed, extending to the proximal extent of the fissure.

Patients were prospectively randomized into one of two groups, before surgery was performed. Randomization was performed in a single blind manner, and determined by coin-toss. Identical tubes of metronidazole 10 wt % in an inert carrier (petrolatum) in accordance with Example 1 and tubes containing the inert carrier (petrolatum) alone, were obtained from a compounding pharmacy. Study patients applied approximately 2.5 $cm^3$ of 10 wt % metronidazole composition to the surgical site three times daily, after a Sitz bath or warm soak. Control patients applied the same quantity of the inert carrier three times a day, after a Sitz bath or warm soak. All patients were supplied with a standard narcotic analgesic (hydrocodone, 10 mg po q 4-6 hrs prn; twenty five tablets dispensed), instructed to take a fiber supplement (Konsyl) twice daily, 30 $cm^3$ mineral oil once daily, and maintain adequate oral hydration.

Postoperative pain was evaluated using a visual analog score (VAS), which was recorded by the patient on days 1, 2, 7, 14, and 28. Patients in both groups ranked the level of pain from 0 (no pain) to 10 (very severe pain). The number of analgesics required (number of hydrocodone pills) per 24 hours, was also recorded by the patient on days 1, 2, 7, 14, and 28. Patients were evaluated at two and four weeks postoperatively, and the completed data sheets were collected at the four-week visit. The mean pain scores for each group were compared using Wilcoxin's Rank sum test. The number of narcotic analgesics required in each group was compared using a two-sample t-test.

Wound healing was evaluated at two weeks, by taking a high quality color digital photograph of the surgical site. At the end of the study, three surgeons independently ranked the 20 surgical incisions in a blinded manner. Incisions were graded in three different categories: A, postoperative incisional edema: B, primary versus secondary wound healing; and C, overall wound healing. For each category (A, B and C), each of the three surgeons ranked the twenty photographs and a mean rank for each photograph was calculated. Thus all twenty photographs had three mean ranks for categories A, B and C. Mean ranking in categories A, B and C were then compared between metronidazole and control groups, using the Mann-Whitney U test.

Twenty patients were prospectively enrolled in the study. Ten patients received 10% metronidazole composition and ten patients receiving the inert carrier. None of the patients were lost to follow-up. The two groups were comparable in terms of age, gender, hemorrhoidal grade and associated fissure in ano. Three patients in the metronidazole group and four patients in the control group had a fissure in ano, and underwent fissurectomy and sphincterotomy, in addition to hemorrhoidectomy.

There was no significant difference in pre-operative pain scores, or pain scores on days 1 and 2, between the metronidazole an control groups. Metronidazole patients experienced significantly less pain on days 7 and 14, compared to patients in the control group ($P<0.01$ and $P<0.05$ respectively). There was no significant difference between groups on day 28. There was no significant difference in narcotic requirements between metronidazole and control groups on postoperative days 1 and 2. Metronidazole patients required significantly fewer narcotic analgesics on day 7, compared to control patients ($P<0.05$). There was no significant difference between groups on days 14 and 28.

Wound healing in the metronidazole group was significantly better than controls, when ranked according to category A, postoperative edema ($P<0.01$) and category C, overall healing ($P<0.05$). There was no difference between groups when incisions were ranked according to category B, primary versus secondary healing ($P>0.05$).

Example 3—Refractory Anorectal Crohn's Disease

A prospective pilot study of topical 10 wt % metronidazole according to Example 1 in the treatment of refractory anorectal Crohn's disease was undertaken. Three patients are described: one patient was suspected to have the disease on initial examination (Patient 1), and two unsuspected cases were diagnosed after undergoing routine anorectal surgery. Granulomata were identified histologically in all three patients.

Patient 1, a 36 year-old male, presented with anorectal bleeding and mucous discharge, from a fissure-in-ano in the anterior midline. Anorectal Crohn's disease was suspected. Examination under anesthesia and intra-operative colonoscopy revealed a normal appearing colon and a granulomatous fissure, which was biopsied. No additional procedure was undertaken. Histopathology of the biopsy confirmed the presence of non-caseating granulomata. The patient was started immediately on topical 10% metronidazole according to Example 1.

Patient 2, a 78 year-old female, presented with rectal bleeding from prolapsing internal hemorrhoids, with external components. The patient had had a normal barium enema approximately three years previously. The patient failed to respond to fiber supplements and increasing fluid intake, and therefore, surgical hemorrhoidectomy was recommended. Preoperative flexible sigmoidoscopy revealed no evidence of Crohn's disease in the rectum or distal sigmoid.

The patent underwent a three-quadrant closed hemorrhoidectomy for innocuous-appearing hemorrhoidal disease. Histopathology of the hemorrhoidectomy specimens subsequently revealed the presence of non-caseating granulomata. Postoperatively, the patient experienced severe pain from her incisions, which appeared indurated, granulomatous, and failed to heal. The patient was started on topical 10% metronidazole according to Example 1 three times a day in an attempt to control her pain and heal her incisions.

Patient 3, a 78 year-old female, presented with rectal bleeding and fissure-type symptoms. A posterior midline fissure was noted in association with a sentinel tag. The patient was treated with fiber supplements and copious liquids but failed to respond after two weeks. Intraoperative colonoscopy and examination under anesthesia were performed, which showed a normal appearing colon and a deep posterior midline fissure and a left postero-lateral transsphincteric fistula. The fissure was cauterized, the postero-lateral internal sphincter was divided, and a seton placed through the remaining fistula.

Histopathology of the debrided tissue reported the presence of non-caseating granulomata, consistent with anorectal Crohn's disease. The patient experienced excessive postoperative pain associated with induration, bleeding, and non-healing of the surgical site. Topical 10 wt % metronidazole according to Example 1 was initiated in an attempt to promote healing and control pain.

All three patients experienced dramatic relief of their anorectal pain, and the postoperative induration and granulation tissue resolved significantly within three weeks of starting topical metronidazole. Two patients (Patients 2 and 3) had been started on oral Flagyl for a brief period, but had developed nausea and failed to improve; the medication was discontinued before starting topical metronidazole. No patient was taking any additional antibiotic, anti-inflammatory or immunosuppressive medication.

Patient 1 had anterior anal fissure. After two weeks of topical metronidazole, the patient reported a significant improvement in his pain and anorectal discharge. Repeat examination under anesthesia was performed three weeks later, and the tissue edema and granulomation tissue had resolved dramatically. In addition, the granulomata noted on the initial biopsy had resolved, and none was seen in the second biopsy specimen, performed after 3 weeks of topical metronidazole.

Patient 2 reported dramatic pain relief, and healing of her incisions had progressed significantly after 2 weeks of topical metronidazole treatment. Four weeks later, the patient was asymptomatic from her anorectal disease.

Similarly, Patient 3 experienced dramatic pain relief within two weeks treatment with topical metronidazole and the incisions appeared much improved. At 4 weeks, the granulation tissue and induration had resolved and the seton was therefore removed. At 6 weeks, the incisions were healed, there was no evidence of a persistent fistula, and the patient had no anorectal symptoms.

No patient experienced side effects from topical metronidazole. Two patients (Patients 2 and 3) developed a mildly reddened, shiny appearance of the perianal skin, which resulted in no adverse symptoms.

It will be appreciated that the invention is not restricted to the details described above with reference to the preferred embodiments but that numerous modifications and variations can be made without departing from the spirit or scope of the invention as defined in the following claims.

The invention claimed is:

1. A method of relieving pain or promoting wound healing in a patient following a surgical operation to the colon, rectum, anorectum or perianal region of patient, said method comprising:
    applying directly to the colon, rectum, anorectum or perianal region of patient affected by the surgical operation a topical composition, wherein the topical composition consists essentially of metronidazole in a therapeutically effective concentration of 10 wt % in a pharmacologically acceptable non-aqueous vehicle, wherein metronidazole is the sole active agent in said topical composition for relieving pain or promoting wound healing in the patient.

2. The method of claim 1 for relieving pain following said surgical operation.

3. The method of claim 1 for promoting wound healing following said surgical operation.

4. The method of claim 1 for relieving pain and promoting wound healing following said surgical operation.

5. The method of claim 1, wherein the topical composition reduces edema.

6. The method of claim 1, wherein the topical composition reverses tissue induration and granulation.

7. The method of claim 1, wherein the topical composition reduces anorectal discharge.

8. The method of claim 1, wherein the surgical operation is an anorectal operation.

9. The method of claim 1, wherein the surgical operation is selected from the group consisting of a hemorrhoidectomy, a fistulotomy, a fissurectomy, a sphincterotomy, sphincteroplasty, or incision and drainage of an abscess, and excision of pilonidal abscess or sinus.

10. The method of claim 1, wherein the surgical operation is a hemorrhoidectomy.

11. The method of claim 1, wherein said patient suffers from perianal Crohn's disease.

12. The method of claim 1, wherein said vehicle is an organic vehicle.

13. The method of claim 1, wherein the vehicle comprises at least one hydrocarbon compound.

14. The method of claim 1, wherein the vehicle comprises a mixture of at least two semi-solid saturated hydrocarbon compounds.

15. The method of claim 1, wherein the vehicle comprises white petrolatum (USP).

16. The method of claim 1, wherein said topical composition is in a form suitable for direct application to the colon, rectum, anorectum, perianal region or anal canal.

17. The method of claim 1, wherein said topical composition is in the form of an enema, suppository, ointment, lotion, gel, foam or cream.

18. The method of claim 1, wherein said topical composition is in the form of an ointment.

19. The method of claim 1, wherein metronidazole is applied at a dosage for each application from about 125 mg to about 1250 mg.

20. The method of claim 19, wherein the dosage of metronidazole for each application is from about 125 mg to about 375 mg.

21. The method of claim 19, wherein the dosage of metronidazole for each application is about 250 mg.

22. The method of claim 1, wherein said topical composition is applied between from 2 to 4 times daily.

23. The method of claim 1, wherein said topical composition is applied 3 times daily.

24. The method of claim 1, wherein said topical composition has a fluffy texture.

25. The method of claim 24, wherein said topical composition is obtained by passing metronidazole and white petrolatum through an ointment mill.

* * * * *